(12) United States Patent
Muramatsu et al.

(10) Patent No.: US 9,772,277 B2
(45) Date of Patent: Sep. 26, 2017

(54) GAS ABSORPTION SPECTROSCOPIC SYSTEM AND GAS ABSORPTION SPECTROSCOPIC METHOD

(71) Applicant: SHIMADZU CORPORATION, Kyoto-shi, Kyoto (JP)

(72) Inventors: Takashi Muramatsu, Uji (JP); Naoji Moriya, Nara (JP); Naoki Matsuda, Nara (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 14/758,900

(22) PCT Filed: Dec. 25, 2013

(86) PCT No.: PCT/JP2013/084741
§ 371 (c)(1),
(2) Date: Jul. 1, 2015

(87) PCT Pub. No.: WO2014/106940
PCT Pub. Date: Jul. 10, 2014

(65) Prior Publication Data
US 2015/0338342 A1  Nov. 26, 2015

(30) Foreign Application Priority Data
Jan. 7, 2013 (JP) .................... 2013-000305

(51) Int. Cl.
*G01N 21/39* (2006.01)
*G01N 21/31* (2006.01)
(Continued)

(52) U.S. Cl.
CPC .............. *G01N 21/39* (2013.01); *G01J 3/027* (2013.01); *G01J 3/42* (2013.01); *G01N 21/3103* (2013.01);
(Continued)

(58) Field of Classification Search
CPC .............. G01N 21/39; G01N 21/3103; G01N 21/3504; G01N 2201/0612; G01N 21/274;
(Continued)

(56) References Cited

U.S. PATENT DOCUMENTS 5,284,137 A * 2/1994 Kessler ................ G01N 21/314
  128/898
5,317,156 A * 5/1994 Cooper .................. G01N 21/39
  250/339.13

(Continued)

FOREIGN PATENT DOCUMENTS

CN  1201905 A   12/1998
CN  101331391 A  12/2008
(Continued)

OTHER PUBLICATIONS

"Reconstruction of the first derivative EPR spectrum from multiple harmonics of the field-modulated continuous wave signal" to Tseitlin et al. (J Magn Reson. Apr. 2011; 209 (2): 277-281).*

(Continued)

*Primary Examiner* — Tarifur Chowdhury
*Assistant Examiner* — Mohamed K Amara
(74) *Attorney, Agent, or Firm* — Sughrue Mion, PLLC (57) ABSTRACT

Provided is a gas absorption spectroscopic system and gas absorption spectroscopic method capable of accurately measuring the concentration or other properties of gas even in high-speed measurements. Laser light with a varying wavelength is cast into target gas. A spectrum profile representing a change in the intensity of the laser light transmitted through the target gas with respect to wavelength is determined. For this spectrum profile, polynomial approximation is performed at each wavelength point within a predetermined wavelength width, using an approximate polynomial.

(Continued)

Based on the coefficients of the terms in the approximate polynomial at each point, an nth order derivative curve, where n is an integer of zero or larger, of the spectrum profile is created. A physical quantity of the target gas is determined based on the thus created nth order derivative curve.

9 Claims, 4 Drawing Sheets

(51) Int. Cl.
*G01J 3/42* (2006.01)
*G01J 3/02* (2006.01)
G01N 21/3504 (2014.01)

(52) U.S. Cl.
CPC . *G01N 21/3504* (2013.01); *G01N 2201/0612* (2013.01)

(58) Field of Classification Search
CPC ........... G01N 2021/399; G01N 21/359; G01N 21/031; G01N 21/314; G01N 21/31; G01N 21/255; G01N 21/59; G01N 21/27; G01N 33/225; G01J 3/027; G01J 3/42; G01J 3/02; G01J 3/10; G01J 3/32; G01J 3/12; G01J 2003/423; G01J 3/524
USPC ..................................................... 702/28, 23
See application file for complete search history.

(56) References Cited

U.S. PATENT DOCUMENTS

| | | | | |
|---|---|---|---|---|
| 5,533,509 | A * | 7/1996 | Koashi | A61B 5/14532 356/41 |
| 5,825,579 | A * | 10/1998 | Cheung | G11B 5/59633 360/77.02 |
| 5,957,841 | A | 9/1999 | Maruo et al. | |
| 6,087,182 | A * | 7/2000 | Jeng | G01N 21/05 356/72 |
| 6,429,995 | B1 * | 8/2002 | Dobbek | G11B 5/59655 360/77.08 |
| 6,522,493 | B1 * | 2/2003 | Dobbek | G11B 5/59627 360/75 |
| 7,217,574 | B2 * | 5/2007 | Pien | B01L 3/5085 436/164 |
| 8,644,911 | B1 * | 2/2014 | Panasyuk | A61B 5/0075 600/473 |
| 2001/0049689 | A1 * | 12/2001 | Mentzer | G06F 19/28 |
| 2004/0208385 | A1 * | 10/2004 | Jiang | A61B 5/0059 382/254 |
| 2004/0230387 | A1 * | 11/2004 | Bechhoefer | G01R 31/11 702/58 |
| 2005/0036144 | A1 * | 2/2005 | Suzuki | G03F 9/7092 356/401 |
| 2006/0013454 | A1 * | 1/2006 | Flewelling | G06K 9/4652 382/128 |
| 2006/0293873 | A1 * | 12/2006 | Gardner | G06F 19/12 703/11 |
| 2008/0255769 | A1 * | 10/2008 | Zhou | G01N 21/3504 702/24 |
| 2009/0048528 | A1 * | 2/2009 | Hopenfeld | A61B 5/0031 600/516 |
| 2009/0076368 | A1 * | 3/2009 | Balas | A61B 1/00149 600/407 |
| 2009/0112484 | A1 * | 4/2009 | Boles | G06F 19/20 702/23 |
| 2009/0164138 | A1 | 6/2009 | Goto et al. | |
| 2010/0030081 | A1 * | 2/2010 | Masuzawa | A61B 8/4483 600/459 |
| 2010/0079602 | A1 * | 4/2010 | Napper | G02B 7/023 348/208.1 |
| 2010/0164029 | A1 * | 7/2010 | Tennant | G01J 3/02 257/432 |
| 2010/0205124 | A1 * | 8/2010 | Ben-Hur | G06K 9/6215 706/12 |
| 2010/0283785 | A1 * | 11/2010 | Satulovsky | G01N 27/447 345/440 |
| 2011/0084769 | A1 * | 4/2011 | Wicpalek | H03L 7/099 331/34 |
| 2011/0106547 | A1 * | 5/2011 | Toraichi | G10L 19/0208 704/501 |
| 2012/0236291 | A1 | 9/2012 | Pittaro et al. | |
| 2014/0340684 | A1 * | 11/2014 | Edler | G01J 3/4338 356/409 |
| 2015/0141854 | A1 * | 5/2015 | Eberle | A61B 5/02154 600/488 |
| 2015/0192507 | A1 * | 7/2015 | Cottet | G01N 35/085 702/29 |
| 2015/0226665 | A1 * | 8/2015 | Weidmann | G01J 3/42 356/437 |
| 2016/0054596 | A1 * | 2/2016 | Lee | G02F 1/025 385/3 |

FOREIGN PATENT DOCUMENTS

| | | |
|---|---|---|
| CN | 101611323 A | 12/2009 |
| EP | 0 869 348 A2 | 10/1998 |
| EP | 1 965 194 A1 | 9/2008 |
| EP | 2 062 056 | 5/2009 |
| JP | 2000-222387 A | 8/2000 |
| JP | 2003-149145 A | 5/2003 |
| JP | 2007-163422 A | 6/2007 |
| JP | 2010-505132 A | 2/2010 |
| JP | 2010-66280 A | 3/2010 |
| JP | 2010-164480 A | 7/2010 |
| JP | 2011-13126 A | 1/2011 |
| JP | 2011-196832 A | 10/2011 |
| KR | 10-0268968 B1 | 12/2000 |
| KR | 10-2008-0091144 A | 10/2008 |
| WO | 2007/069786 A1 | 6/2007 |
| WO | 2008/042718 A2 | 4/2008 |

OTHER PUBLICATIONS

E.D. Hinkley et al., "Detection of Air Pollutants with Tunable Diode Lasers", Science, Feb. 19, 1971, pp. 635-639, vol. 171, No. 3972.
J. Reid et al., "Second-Harmonic Detection with Tunable Diode Lasers-Comparison of Experiment and Theory", Appl. Phys., 1981, pp. 203-210, vol. B26.
Joel A. Silver, "Frequency-modulation spectroscopy for trace species detection: theory and comparison among experimental methods", Applied Optics. Feb. 20, 1992, pp. 707-717, vol. 31, No. 6.
Gregory B. Rieker et al., "Calibration-free wavelength-modulation spectroscopy for measurements of gas temperature and concentration in harsh environments", Applied Optics, Oct. 10, 2009, pp. 5546-5560, vol. 48, No. 29.
T. Ferholz et al., "Digital, phase-sensitive detection for in situ diode-laser spectroscopy under rapidly changing transmission conditions", Appl. Phys., 2002, pp. 229-236, vol. B75.
Jonathan T.C. Liu, "Near-Infrared Diode Laser Absorption Diagnostics for Temperature and Species in Engines", Oct. 2004, Ph.D. Dissertation, Dept. of Mechanical Engineering, Stanford University, (Figure 3.12).
"Calculation of molecular spectra with the Spectral Calculator", Jan. 7, 2013, www.spectralcalc.com.
Katsuhiko Fukuzato et al., CO$_2$ Gas Measurement by Diode Laser Absorption Spectroscopy (2nd Report, Detailed Absorption Spectrum Measurement Near 2.0μm and Time-Resolved Temperature Measurement of Combustion Gas), Transactions of the Japan Society of Mechanical Engineers, 2002, pp. 2901-2907, pp. 231-237.
Abraham Savitzky et al., "Smoothing and Differentiation of Data by Simplified Least Squares Procedures", Analytical Chemistry, 1964, pp. 1627-1639, vol. 36, No. 8.
International Search Report for PCT/JP2013/084741 dated Jan. 28, 2014.

(56) References Cited

OTHER PUBLICATIONS

Written Opinion for PCT/JP2013/084741 dated Jan. 28, 2014. [PCT/ISA/237].

* cited by examiner

S1 — LASER RADIATION
S2 — WAVELENGTH SWEEPING
S3 — SPECTRUM PROFILE ACQUISITION
S4 — POLYNOMIAL APPROXIMATION AT EACH POINT
S5 — POLYNOMIAL COEFFICIENTS ACQUISITION
S6 — SPECTRUM PROFILE CREATION
S7 — DETERMINATION OF PHYSICAL PROPERTIES OF TARGET GAS

Fig. 3A

CONVENTIONAL WMS METHOD

Fig. 3B

METHOD ACCORDING TO PRESENT INVENTION

GAS ABSORPTION SPECTROSCOPIC SYSTEM AND GAS ABSORPTION SPECTROSCOPIC METHOD

CROSS REFERENCE TO RELATED APPLICATIONS

This application is a National Stage of International Application No. PCT/JP2013/084741 filed Dec. 25, 2013, claiming priority based on Japanese Patent Application No. 2013-000305 filed Jan. 7, 2013, the contents of all of which are incorporated herein by reference in their entirety.

TECHNICAL FIELD

The present invention relates to a gas absorption spectroscopic system and method for measuring the concentration, temperature, pressure and other properties of target gas, based on a laser light absorption spectrum of the gas. The gas absorption spectroscopic system and method can be applied for contactless high-speed measurement of the concentration, temperature and pressure of gas in the automotive industry. It can also be used for a measurement of combustion gas within a plant furnace or similar gas in high-temperature and high-pressure environments, as well as in various other areas.

BACKGROUND ART

There are three kinds of gas absorption spectroscopy using lasers:
(1) DLAS (Direct Laser Absorption Spectroscopy)
(2) WMS (Wavelength Modulated Spectroscopy)
(3) CRDS (Cavity Ring Down Spectroscopy)

In DLAS, laser light is cast into target gas and detected with a photodetector. In this detection, the wavelength of the laser light cast into the gas is fixed at a specific value to measure the amount of absorption by the gas, or a certain range of the laser wavelength is swept to measure an absorption spectrum of the gas. In the former case, the wavelength of the laser light is fixed at an absorption wavelength of the gas and the absorbance at that wavelength is measured. In the case of sweeping the wavelength range, the wavelength of the laser light is varied over a range including the absorption wavelength of the gas to obtain a spectrum of the gas and determine the magnitude of area of the absorption peak formed by the gas (Non Patent Literature 1).

WMS is similar to the wavelength-sweeping mode of DLAS. However, in WMS, not only the wavelength is swept through a range, but the wavelength is also sinusoidally modulated with a cycle sufficiently shorter than the sweeping cycle (i.e. at an adequately high frequency, which is herein denoted by f). The detector is tuned to detect a higher harmonic wave of frequency f (normally, the second-order harmonic wave), whereby the absorption by the gas can be measured with higher sensitivity than by DLAS (Patent Literature 1; Non Patent Literatures 2, 3 and 4). For detection of the higher harmonic wave, lock-in amplifiers are normally used. Another method has also been proposed in which the detector signal is directly subjected to digital sampling and subsequently analyzed by FFT for synchronous detection of 2f (Non Patent Literature 5).

In CRDS, the target gas is placed in an optical resonator composed of at least two mirrors. As one example, a CRDS using a CW (continuous wave) laser is hereinafter described. The light which has entered the optical resonator is reflected and resonated within the optical resonator, and a large part of light with an amount of energy corresponding to the reflectance of the mirrors on both sides is trapped in the resonator. Meanwhile, light with a trace amount of energy leaks to the outside of the mirrors. Accordingly, in the steady state, a stable amount of light energy is constantly stored in the resonator, while a certain amount of light continuously leaks to the outside of the mirrors. In this state, if the laser radiation is discontinued, the light energy in the resonator decays at a rate corresponding to the amount of light lost from the resonator, which simultaneously causes a decay in the intensity of light leaking to the outside of the mirrors. The decay time depends on the amount of light absorbed by the target gas in the resonator. Using this fact, the amount of absorption by the gas is determined. Although this technique is more sensitive than WMS, it is susceptible to the contamination of the resonator, and furthermore, its dynamic range is generally narrow, since the resonator loss rapidly increases with an increase in the amount of absorption, making the measurement impossible. Additionally, a highly nerve-straining control is needed for finely mode-locking the laser in the resonator or in other tasks.

From the previously described facts, WMS is said to be suitable for industrial gas absorption spectroscopic systems due to its favorable balance of sensitivity and robustness (ease of measurement). By WMS, the gas concentration can be easily calculated from the intensity of the obtained absorption spectrum. Additionally, WMS can be used in an application which can measure the concentration and/or temperature of the gas by using two wavelengths even under an environment in which it is impossible to directly measure the pressure or temperature although the temperature and pressure are constantly changing (Non Patent Literature 4).

CITATION LIST

Patent Literature

Patent Literature 1: JP 2011-196832 A

Non Patent Literature

Non Patent Literature 1: E. D. Hinkley and P. L. Kelley, "Detection of air pollutants with tunable diode lasers," Science 171, 635-639 (1971)

Non Patent Literature 2: Reid, J. and Labrie, D., "Second-harmonic detection with tunable diode lasers-comparison of experiment and theory," Appl. Phys. B 26, 203-210 (1981)

Non Patent Literature 3: J. A. Silver, "Frequency-modulation spectroscopy for trace species detection: theory and comparison among experimental methods,"Appl. Opt. 31, 707-717 (1992)

Non Patent Literature 4: G. B. Rieker, J. B. Jeffries, and R. K. Hanson, "Calibration-free wavelength modulation spectroscopy for measurements of gas temperature and concentration in harsh environments," Appl. Opt. 29, 5546-5560 (2009)

Non Patent Literature 5: T. Fernholz, H. Teichert, and V. Ebert, "Digital, phase-sensitive detection for in situ diode-laser spectroscopy under rapidly changing transmission conditions," Appl. Phys. B 75, 229-236 (2002)

Non Patent Literature 6: J. T. C. Liu, "Near-infrared diode laser absorption diagnostics for temperature and species in engines," Ph.D. dissertation, Dept. Mechanical Engineering, Stanford Univ., Stanford, Calif., 2004. (FIG. 3.12)

Non Patent Literature 7: "Calculation of molecular spectra with the Spectral Calculator", [accessed on Jan. 7, 2013], the Internet Non Patent Literature 8: Katsuhiko Fukuzato, Yuji Ikeda, and Tsuyoshi Nakajima, "$CO_2$ gas measurement by diode laser absorption spectroscopy ($2^{nd}$ Report)", *Transactions of the Japan Society of Mechanical Engineers, Series B* 68, 2901-2907 (2002)

SUMMARY OF INVENTION

Technical Problem

As just described, WMS is a robust and highly sensitive method. However, it has the following problems:

1. For high-speed measurements, WMS requires both a short sweeping cycle and a high wavelength modulation frequency. However, if an injection current control type tunable diode laser (which is the most widely used type of tunable laser) is used as the wavelength-variable laser, increasing the modulation frequency lowers the changing rate of the wavelength with respect to the injection current and makes it impossible to achieve a sufficient modulation depth (Non Patent Literature 6).

2. In particular, for a high-frequency modulation which exceeds MHz levels, it is difficult to accurately measure the modulation depth. That is to say, it is impossible to correctly determine the modulation depth in high-speed measurements. Therefore, the concentration, temperature or other information on the gas calculated from the measured result has a high degree of uncertainty.

Due to the previously described factors, the conventional WMS has the problem that the measurement of the concentration, temperature and other properties of gas becomes noticeably difficult when the measurement is performed at high speeds.

The problem to be solved by the present invention is to provide a gas absorption spectroscopic system and gas absorption spectroscopic method capable of correctly measuring the concentration or other properties of gas even in high-speed measurements.

Solution to Problem

The gas absorption spectroscopic system according to the present invention aimed at solving the previously described problems includes:

a) a wavelength-variable light source;

b) a light source controller for varying the wavelength of light generated by the light source;

c) a photodetector for detecting the intensity of light generated by the light source and transmitted through target gas;

d) a polynomial approximator for creating a curve approximating a change in the intensity of the light detected by the photodetector with a change in the wavelength varied by the light source controller, using an approximate polynomial at each wavelength point and within a predetermined wavelength width;

e) a derivative curve creator for creating an nth order derivative curve, where n is an integer of zero or larger, based on the coefficient of each term of the approximate polynomial at each of the wavelength points; and f) a physical quantity determiner for determining at least one among the temperature, concentration and pressure of the target gas, based on the nth order derivative curve.

The "wavelength" in the present context uniquely corresponds to the "wavenumber." Therefore, it is naturally possible to construct a similar system using the "wavenumber."

In the gas absorption spectroscopic system according to the present invention, the wavelength of the light cast into the target gas (which is normally, but not necessarily, laser light) is varied (i.e. a wavelength range is swept) as in DLAS. However, the light is not modulated as in WMS. The wavelength may be varied (swept) only one time between the lowest and highest predetermined frequencies, or the sweeping may be repeated multiple times.

After passing through the target gas, the light is received by the photodetector and its intensity change is detected. The range of wavelengths to be swept is previously set, including the absorption wavelength of the target gas. Therefore, an absorption peak centering on a wavelength specific to the target gas appears in the spectrum profile of the light detected by the photodetector (this profile corresponds to the "curve representing a change in the intensity of the light detected by the photodetector with a change in the wavelength varied by the light source controller").

In the gas absorption spectroscopic system according to the present invention, a mathematical operation similar to the WMS process is performed on this spectrum profile including the absorption peak. Specifically, an nth order polynomial approximation is performed on the spectrum profile in a section corresponding to the modulation depth of the WMS around each wavelength point, and the amplitude of the WMS signal is reproduced using the coefficients in the nth order polynomial based on the principle of Fourier transform. This principle is as follows.

Regarding the WMS process, it is generally known that a spectrum profile of an nth order harmonic wave obtained by synchronous detection approximately takes the form of an nth order derivative of the absorption spectrum (Non Patent Literature 2: Equation 8). Accordingly, it is possible to consider that a spectrum corresponding to the nth order synchronous detection can be obtained by nth order differentiation of the spectrum obtained by the wavelength sweeping. However, the nth order differentiation has the practical problem that the noise in the measurement data significantly affects the nth order differentiation. To avoid this problem, in the gas absorption spectroscopic system according to the present invention, mth order polynomial approximation is performed over a certain range centering on a wavelength at which the higher harmonic wave needs to be determined. The coefficients in the obtained polynomial correspond to the higher harmonic wave signal which will be obtained by the WMS process. The range over which the polynomial approximation is performed corresponds to the amplitude of modulation in the WMS process.

The higher the order of the approximate polynomial is, the more accurate the approximation is. Normally, the first or second order approximate polynomial is sufficient.

Also performed is a process for correcting a change in the amount of light associated with unwanted factors, such as a blockage of light other than absorption by the gas.

Advantageous Effects of the Invention

In the gas absorption spectroscopic system according to the present invention, since the wavelength sweeping in the light source is performed at a frequency of several hundreds of kHz or lower, the oscillation wavelength of the light source corresponding to the injection current can be accurately determined. Since the WMS process is performed by mathematical operation based on the wavelength information, a high order synchronous detection with a correct modulation depth can be performed without being affected by the non-linearity of the power source for driving the light source or that of the light source itself.

The use of the mathematical process allows simultaneous acquisition of WMS spectra with a plurality of modulation depths using a single light source. This makes it easier to realize a system which has only a single light source yet can perform a temperature measurement which has conventionally required two or more light sources. In temperature measurements, the modulation depth must be optimally adjusted to minimize the pressure dependency of the measured temperature. Conventional techniques require this adjustment to be made before the measurement. By contrast, according to the present invention, the modulation depth can be adjusted in an ex-post analysis.

DESCRIPTION OF EMBODIMENTS

Figure 1:
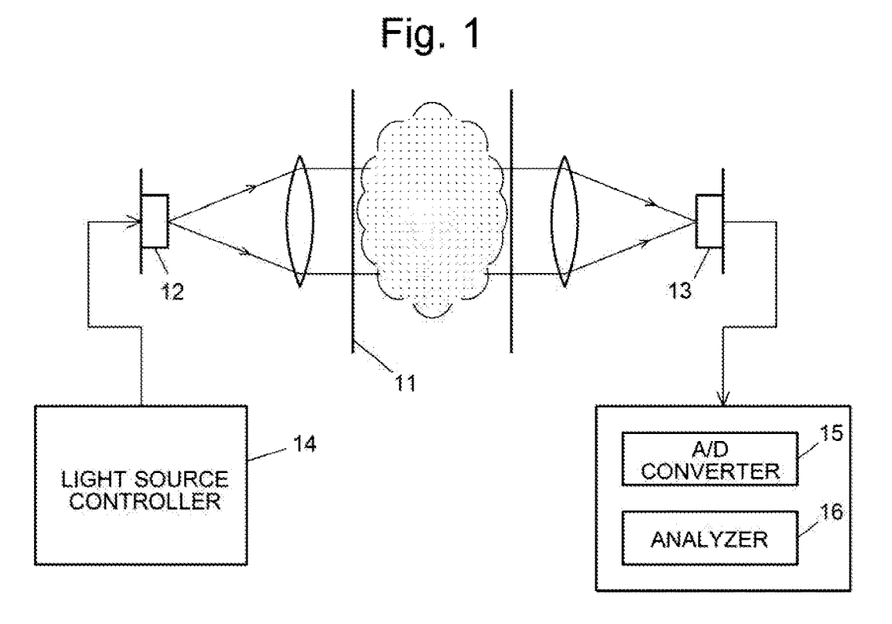
FIG. 1 is a schematic configuration diagram of one embodiment of the gas absorption spectroscopic system according to the present invention.

A schematic configuration of a gas absorption spectroscopic system as one embodiment of the present invention is shown in FIG. 1. A laser source 12 and a photodetector 13 are placed on both sides of a gas cell 11 which contains target gas or through which the target gas is passed. The laser source 12 has a variable wavelength. A light source controller 14 sweeps (varies) this wavelength between the shortest and longest predetermined wavelengths. The photodetector 13 produces an electric signal which shows the intensity of light. This signal is subjected to digital sampling by an A/D converter 15 and sent to an analyzer 16.

Figure 2:
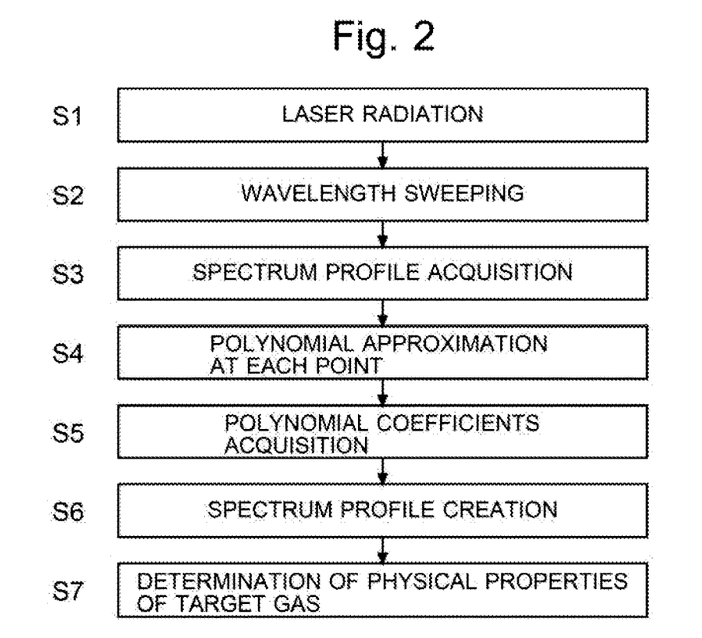
FIG. 2 is a flowchart showing a procedure for measuring the concentration and other properties of target gas according to the present invention.
Figure 3A:
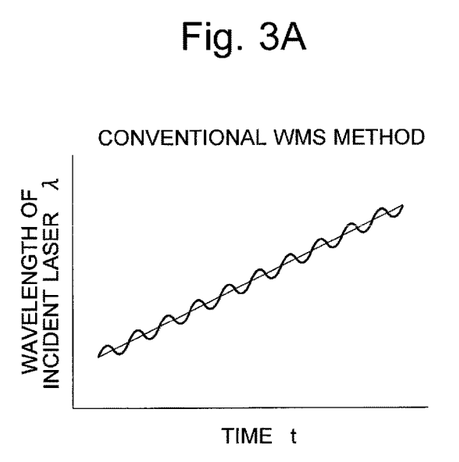
FIG. 3A is a graph showing the form of a change in the wavelength of the laser source in a conventional WMS method.
Figure 3B:
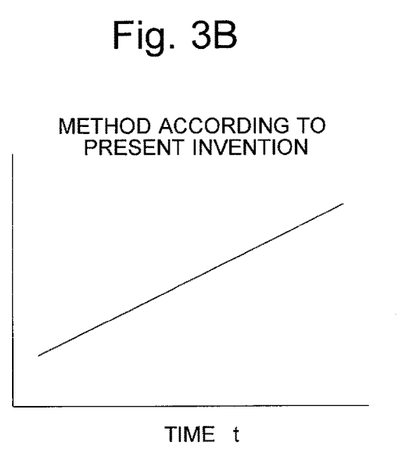
FIG. 3B is a corresponding graph in the case of a method according to the present invention.

A procedure for measuring the concentration, temperature, pressure and other properties of the target gas is as follows (FIG. 2): The light source controller 14 operates the laser source 12 to radiate laser light having the shortest predetermined wavelength (Step S1) and then sequentially varies the wavelength to the longest wavelength (Step S2). As already noted, in the conventional WMS method, while the wavelength is varied (swept), the wavelength is modulated with a predetermined wavelength width, as shown in FIG. 3A. In the method according to the present invention, no such modulation is performed, as shown in FIG. 3B. The light from the laser source 12 passes through the target gas in the gas cell 11, where the light undergoes absorption at wavelengths specific to the target gas. The intensity of the laser light transmitted through the target gas is detected by the photodetector 13. The electric signal produced by the photodetector 13, which shows the intensity of the light, is digitized by the A/D converter 15 and sent to the analyzer 16. The change in this electric signal forms the aforementioned spectrum profile (Step S3). Based on the data representing this spectrum profile, the analyzer 16 performs the following mathematical operations.

The mathematical operations performed by the analyzer 16 using a polynomial approximation of the detection signal are hereinafter described and compared to the process performed in the conventional WMS. A spectrum profile centering on an absorption peak of $CO_2$ obtained from the HITRAN 2008 database has been used as the gas absorption spectrum to be processed. Naturally, the following operations should actually be performed on a spectrum profile obtained in the previously described manner.

For this spectrum, the polynomial approximation was performed by the analyzer 16 of the gas absorption spectroscopic system according to the present invention, and the obtained result was compared with a result obtained by simulating a lock-in amplifier based on the conventional WMS process.

Figure 4:
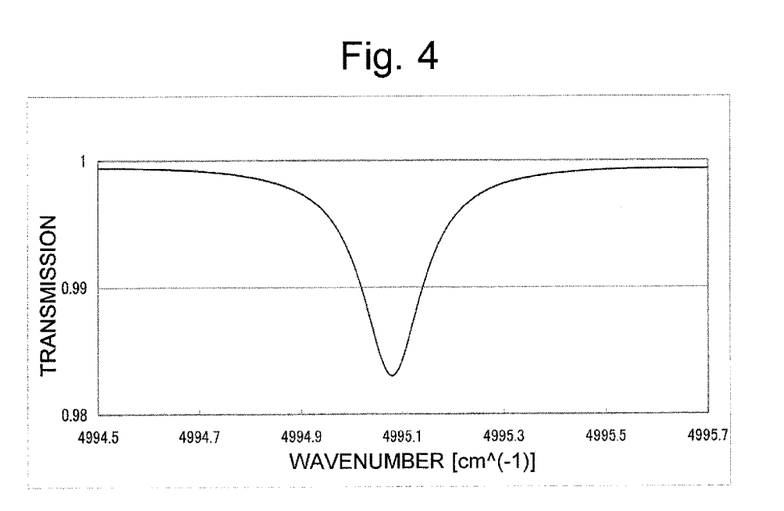
FIG. 4 is the profile of a gas transmission spectrum used for verifying the present invention.

FIG. 4 shows the transmission profile used in the simulation. This has been obtained by simulating a gas cell with an optical length of 5 cm under the conditions of 3% $CO_2$ concentration and 1-atm pressure, paying attention to an absorption line near 2 μm (5000 cm$^{-1}$).

It is generally known that an absorption peak under atmospheric pressure can be expressed by the following Lorentzian function:

$$g(v) = \frac{A}{\pi} \frac{\alpha_L}{(v - v_c)^2 + \alpha_L^2} \quad (1)$$

where v is the wavenumber, A is the peak area, $v_c$ is the wavenumber of the peak, and $\alpha_L$ is the half width at half maximum of the Lorentz broadening.

Consider the situation where incident laser light which has been modulated with amplitude a according to the WMS method is passing through gas having the aforementioned absorption profile. If synchronous detection of this gas using a lock-in amplifier is performed, the spectrum obtained by the nth order synchronous detection will be expressed by the following equation (Non Patent Literature 2):

$$H_n(\bar{v}) = \frac{1}{\pi} \int_{-\pi}^{\pi} \tau(\bar{v} + a\cos(\theta))\cos(n\theta) d\theta, n \geq 1 \quad (2)$$

where $\bar{v}$ is the wavenumber, τ is the profile of the transmission spectrum and a is the amplitude of modulation.

Figure 6:
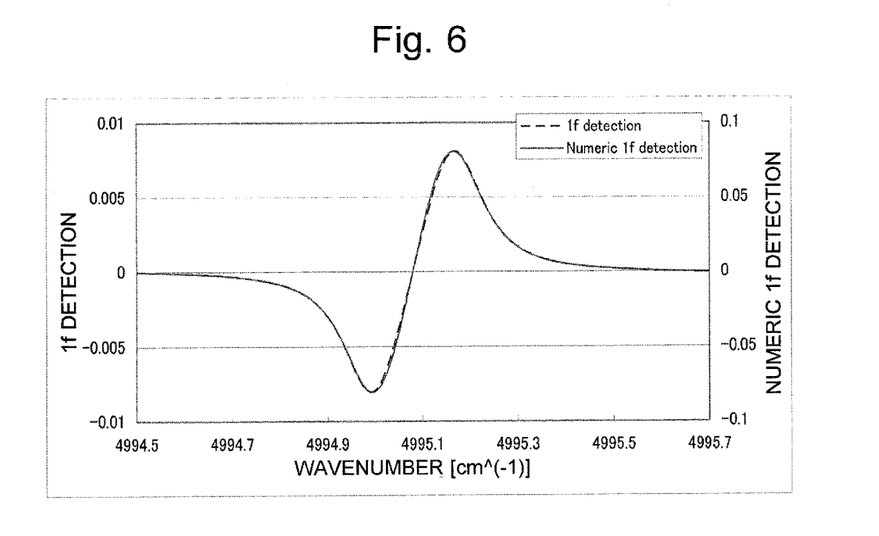
FIG. 6 is a graph showing a first order synchronous detection profile (broken line) and a first order derivative profile (solid line) calculated by the method according to the present invention (using a second order polynomial).
Figure 7:
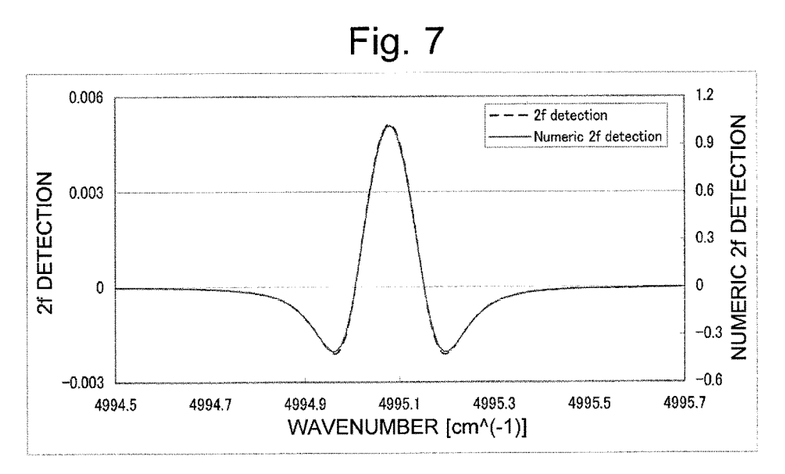
FIG. 7 is a graph showing a second order synchronous detection profile (broken line) and a second order derivative profile (solid line) calculated by the method according to the present invention (using a second order polynomial).

The broken lines in FIGS. 6 and 7 respectively show the profiles obtained by the first order (n=1; which is hereinafter referred to as "1f") and second order (n=2; which is hereinafter referred to as "2f") synchronous detections with a=0.1 cm$^{-1}$ actually performed on the profile shown in FIG. 4.

Although equation (2) in the present form may also be used to perform a mathematical operation equivalent to the WMS process, it is too complex for practical use. Accordingly, in the present invention, a polynomial is used in the mathematical operation to perform a process equivalent to high order (including the zeroth order) detections of WMS in a faster and simpler way and then measure various physical quantities of the target gas.

In the method according to the present invention, it is initially assumed that a range centering on each point v with a width of 2a', [$\bar{v}-a'<v<\bar{v}+a'$], on the wavenumber axis of the profile of a spectrum obtained by DLAS is expressed by the following polynomial:

$$\tau(v) = b_0 + b_1(v-\bar{v}) + b_2(v-\bar{v})^2 + b_3(v-\bar{v})^3 + \ldots \quad (3)$$

Figure 5:
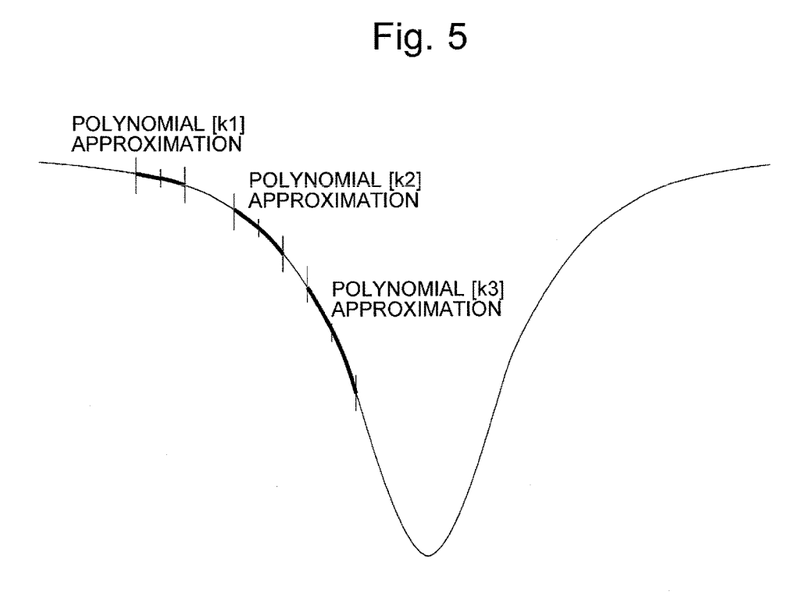
FIG. 5 is a model diagram illustrating how to represent a spectrum profile using a polynomial.

FIG. 5 schematically illustrates this. The nth order derivative of equation (3) is:

$$\frac{d^n \tau(v)}{dv^n}\bigg|_{v=\bar{v}} = b_n \quad (4)$$

Meanwhile, it is generally known that the spectrum profile of an nth order harmonic wave obtained by synchronous detection in the WMS process can be approximately expressed by the following equation (Non Patent Literature 2: Equation 8):

$$H_n(\bar{v}) \approx \frac{2^{1-n} \tau(v)}{n!} a^n \frac{d^n \tau(v)}{dv^n}\bigg|_{v=\bar{v}}, n \geq 1 \quad (5)$$

From equations (4) and (5):

$$H_n(\bar{v}) \approx \frac{2^{1-n} \tau(v)}{n!} a^n b_n, n \geq 1 \quad (6)$$

Accordingly, to calculate the WMS signal for wavenumber $\bar{v}$ in the DLAS spectrum, a function which fits the curve within the wavenumber range [$\bar{v}-a'<v<\bar{v}+a'$] is determined by the least squares method or similar method (Step S4), and the coefficients $b_0$, $b_1$, $b_2$, $b_3$ ... are determined (Step S5). The profiles of the coefficients $b_1$ and $b_2$ determined by the curve fitting while sequentially changing $\bar{v}$ respectively correspond to the 1f and 2f WMS profiles (Step S6). The value a' representing the range of fitting corresponds to the amplitude of modulation.

In the present example, for the profile shown in FIG. 4, the polynomial was terminated at the second order term. The solid lines in FIGS. 6 and 7 respectively show the coefficients $b_1$(1f) and $b_2$(2f) plotted against the wavenumber $\bar{v}$. The fitting range is a'=0.11 cm$^{-1}$.

Figure 8:
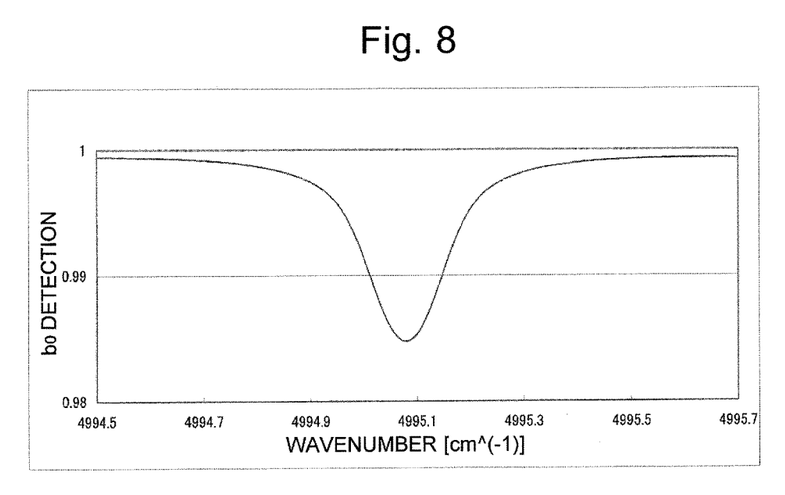
FIG. 8 is a spectrum profile created as a result of plotting coefficient $b_0$ against wavenumber "$\bar{v}$".

A comparison of the profiles obtained by equations (2) and (3) demonstrates that the two profiles have considerably similar shapes except for the difference in the scale of the vertical axis. The error due to the termination at the second order term is also adequately small. The difference in the scale is evident from equation (6). Additionally, FIG. 8 shows the coefficient $b_0$ plotted against the wavenumber $\bar{v}$. The profile in FIG. 8 is roughly identical to the DLAS spectrum shown in FIG. 4. This is evident from the fact that substituting $v=\bar{v}$ into equation (3) gives $\tau(\bar{v})=b_0$.

In an actual measurement of target gas, the concentration, pressure, temperature and other properties of the gas are calculated based on the high order derivative curves (including the zeroth order) thus created (Step S7). For example, the concentration of the target gas can be calculated from the area of the absorption peak of the zeroth order derivative curve (FIG. 8). It may also be calculated from the peak height of the second order derivative curve (FIG. 7). The pressure P of the target gas is known to have the following relationship with the half width at half maximum $\alpha_L$ of the absorption peak of the zeroth order derivative curve (FIG. 8) (Non Patent Literature 7):

$$\alpha_L = \alpha_{L0}\left(\frac{P}{P_0}\right)\left(\frac{T_0}{T}\right)^\gamma \quad (7)$$

where $\alpha_{L0}$ is the half width at half maximum at pressure $P_0$ and temperature $T_0$, $P_0$ is the pressure of the target gas at a reference point in time, T is the temperature of the target gas at the point in time of the measurement, To is the temperature at the reference point in time, and $\gamma$ is the constant representing the temperature dependency of the Lorentz width.

From this equation, the pressure of the target gas can be determined.

As for the temperature of the target gas, it is generally known that the ratio of the sizes of two absorption peaks varies with the temperature. This relationship can be used to detect the temperature of the target gas (Non Patent Literature 8).

In actual measurements, the DLAS spectrum obtained by the measurement contains shot noise from the photodetector and electrical noise from the amplifier circuits. In the method according to the present invention, since the curve fitting is achieved by mathematical operations, the 1f and 2f WMS profiles as well as the DLAS spectrum can be obtained with a reduced amount of noise.

Next, a process for normalizing the intensity of the transmitted light is described.

One of the practical problems related to gas absorption spectroscopy is the change in the light intensity associated with a shift of the optical axis due to the contamination of optical parts used in the gas cell or the vibration which occurs under unfavorable environments. Therefore, a process for correcting the light intensity is required. One commonly known correction method is the normalization in which the 2f signal obtained by synchronous detection is divided by the 1f signal (Non Patent Literature 4). However, this method requires modulating the laser light as well as providing two synchronous detection circuits for 1f and 2f, respectively.

By contrast, the WMS-equivalent process using the polynomial approximation according to the present invention requires neither the modulation of the laser light nor the synchronous detection circuits. Furthermore, since the 1f and 2f detection signals can be simultaneously calculated in the approximation process, the normalization can be performed effortlessly. A detailed description follows.

Let $I_0$ denote the intensity of the incident light to gas. Then, the intensity of the detected light is expressed as $S(v)=GI_0\tau(v)$, where G represents the electrical gain for the decrease (and fluctuation) in the light intensity by the optical parts and the intensity of the detected light. For an actual system, by applying the WMS process using the mathematical operation to $S(v)$, the following equation is obtained:

$$S(v) = b_0' + b_1'(v-\bar{v}) + b_2'(v-\bar{v})^2 + b_3'(v-\bar{v})^3 + \ldots \quad (8)$$

Accordingly, the coefficients obtained in this step are:

$$b_0' = GI_0 b_0 \quad (9a)$$

$$b_1' = GI_0 b_1 \quad (9b)$$

$$b_2' = GI_0 b_2 \quad (9c)$$

A value which only depends on the transmission spectrum and is independent of the fluctuation in the light intensity can be obtained by dividing $b_2'$ (2f signal) by $b_1'$ (1f signal) or $b_0'$ as follows:

$$\frac{b_2'}{b_1'} = \frac{b_2}{b_1} \quad (10a)$$

$$\frac{b_2'}{b_0'} = \frac{b_2}{b_0} \approx b_2 \quad (10b)$$

If the absorption is low, then $b_0 \sim 1$ (i.e. $b_0$ is close to 1), so that an approximation as shown by equation (10b) is available. As a result, a robust gas measurement which is independent of the light intensity is made possible.

REFERENCE SIGNS LIST

11 ... Gas Cell
12 ... Laser Source
13 ... Photodetector
14 ... Light Source Controller
15 ... A/D Converter
16 ... Analyzer

The invention claimed is:

1. A gas absorption spectroscopic system, comprising:
 a) a wavelength-variable light source;
 b) a light source controller for varying a wavelength of light generated by the light source;
 c) a photodetector for detecting an intensity of light generated by the light source and transmitted through target gas;
 d) a polynomial approximator for creating a curve approximating a change in the intensity of the light detected by the photodetector with a change in the wavelength varied by the light source controller, using a plurality of discrete approximate polynomials, each of the plurality of approximate polynomials being centered at a respective wavelength point within a predetermined wavelength width, the predetermined wavelength width corresponding to a modulation depth of a Wavelength Modulation Spectroscopy—WMS—signal;
 e) a derivative curve creator for creating an nth order derivative curve, where n is an integer of zero or larger, based on a coefficient of each term of the approximate polynomial at each of the wavelength points; and
 f) a physical quantity determiner for determining at least one among the temperature, concentration and pressure of the target gas, based on the nth order derivative curve'.

2. The gas absorption spectroscopic system according to claim 1, wherein the approximate polynomials used in the polynomial approximator are second order polynomials.

3. The gas absorption spectroscopic system according to claim 2, wherein a zeroth order derivative curve is used in the polynomial approximator and the derivative curve creator, and the concentration of the target gas is determined from a peak area of the zeroth order derivative curve in the physical quantity determiner.

4. The gas absorption spectroscopic system according to claim 2, wherein the created nth order derivative curve is a second order derivative curve, and the concentration of the target gas is determined from a peak height of the second order derivative curve in the physical quantity determiner.

5. The gas absorption spectroscopic system according to claim 1, wherein a zeroth order derivative curve is used in the polynomial approximator and the derivative curve creator, and the concentration of the target gas is determined from a peak area of the zeroth order derivative curve in the physical quantity determiner.

6. The gas absorption spectroscopic system according to claim 1, wherein a second order derivative curve is used in the polynomial approximator and the derivative curve creator, and the concentration of the target gas is determined from a peak height of the second order derivative curve in the physical quantity determiner.

7. The gas absorption spectroscopic system according to claim 6, wherein a normalization for correcting a fluctuation in an amount of light is performed on the second order derivative curve in the derivative curve creator by dividing the coefficient of the second order term of the approximate polynomial at each of the wavelength points by the coefficient of the first order term or the coefficient of the zeroth order term.

8. A gas absorption spectroscopic method, comprising steps of:
 a-1) casting light with a varying wavelength into target gas;
 a-2) detecting an intensity of light transmitted through the target gas;
 b) performing a polynomial approximation of creating a curve approximating a change in the intensity of the light transmitted through the target gas with respect to the wavelength, using a plurality of discrete approximate polynomials, each of the plurality of approximate polynomials being centered at a respective wavelength point within a predetermined wavelength width, the predetermined wavelength width corresponding to a modulation depth of a Wavelength Modulation Spectroscopy—WMS—signal;
 c) creating an nth order derivative curve, where n is an integer of zero or larger, based on a coefficient of each term of the approximate polynomial at each of the wavelength points; and
 d) determining a physical quantity of the target gas based on the nth order derivative curve.

9. The gas absorption spectroscopic method according to claim 8, further comprising a step of performing a normalization process for correcting a fluctuation in an amount of light by dividing the coefficient of the second order term of the approximate polynomial at each of the wavelength points by the coefficient of the first order term or the coefficient of the zeroth order term, wherein the nth order derivative curve is a second order derivative curve and the normalization process is performed on the second order derivative curve.

* * * * *